(12) United States Patent
Kantner et al.

(10) Patent No.: US 6,433,073 B1
(45) Date of Patent: Aug. 13, 2002

(54) POLYURETHANE DISPERSION IN ALCOHOL-WATER SYSTEM

(75) Inventors: Steven S. Kantner, St. Paul; Matthew T. Scholz, Woodbury; Kevin M. Lewandowski, Inver Grove Heights, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/626,028

(22) Filed: Jul. 27, 2000

(51) Int. Cl.[7] .............................. C08J 3/03; C08J 3/09; C08G 18/40; A61K 7/06; A61K 7/043
(52) U.S. Cl. ...................... 524/591; 424/59; 424/61; 424/63; 424/64; 424/69; 424/70.1; 424/70.7; 424/70.11; 424/78.37; 424/401; 424/405; 524/839; 524/840; 528/71
(58) Field of Search ................... 524/591, 839, 524/840; 528/71; 424/59, 61, 63, 64, 69, 70.1, 70.7, 70.11, 78.37, 401, 405

(56) References Cited

U.S. PATENT DOCUMENTS

| | | | |
|---|---|---|---|
| 3,479,310 A | 11/1969 | Dieterich et al. | 524/591 |
| 3,600,359 A | 8/1971 | Miranda | 558/240 |
| 3,700,643 A | 10/1972 | Smith et al. | 526/282 |
| 4,307,219 A | 12/1981 | Larson | 528/71 |
| 4,423,179 A | 12/1983 | Guagliardo | 524/539 |
| 4,507,430 A | 3/1985 | Shimada et al. | 524/839 |
| 4,667,661 A | 5/1987 | Scholz et al. | 128/90 |
| 4,699,133 A | 10/1987 | Schafer et al. | 128/156 |
| 4,738,992 A | 4/1988 | Larson et al. | 521/157 |
| 5,045,601 A * | 9/1991 | Capelli et al. | 525/327.1 |
| 5,230,701 A | 7/1993 | Meyer et al. | 602/76 |
| 5,326,815 A | 7/1994 | Serdiuk et al. | 524/591 |
| 5,334,650 A | 8/1994 | Serdiuk et al. | 524/591 |
| RE34,730 E | 9/1994 | Salatin et al. | 427/407.1 |
| 5,370,910 A | 12/1994 | Hille et al. | 427/407.1 |
| 5,616,400 A | 4/1997 | Zhang | 428/195 |
| 5,626,840 A | 5/1997 | Thomaides et al. | 424/70.11 |
| 5,643,581 A | 7/1997 | Mougin et al. | 424/401 |
| 5,672,653 A | 9/1997 | Frisch et al. | 524/591 |
| 5,679,754 A | 10/1997 | Larson et al. | 528/28 |
| 5,692,937 A | 12/1997 | Zhang | 442/149 |
| 5,843,523 A | 12/1998 | Mazza et al. | 427/208.8 |
| 5,874,072 A | 2/1999 | Alwattari et al. | 424/70.7 |
| 5,951,993 A | 9/1999 | Scholz et al. | 424/405 |
| 5,968,494 A | 10/1999 | Kukkala et al. | 424/70.1 |
| 5,972,354 A | 10/1999 | de la Poterie et al. | 424/401 |
| 5,981,650 A | 11/1999 | Zhao et al. | 524/591 |

FOREIGN PATENT DOCUMENTS

| | | |
|---|---|---|
| EP | 0 416 659 | 3/1991 |
| EP | 656021 B1 | 2/1994 |
| EP | 0 590 480 | 4/1994 |
| EP | 938889 A2 | 9/1999 |
| WO | WO96/14049 | 5/1996 |
| WO | WO99/43289 | 2/1999 |

OTHER PUBLICATIONS

C. R. Noller, *Chemistry of Organic Compounds*, Ch. 6, pp. 121–122 (1957).

* cited by examiner

Primary Examiner—Rabon Sergent

(57) ABSTRACT

A polyurethane dispersion and a method of making are provided. The polyurethane dispersion is stable in a mixture of alcohol and water. The dispersion comprises the reaction product of (a) an isocyanate terminated polyurethane prepolymer comprising the reaction product of (i) at least one oligomeric polyactive hydrogen compound insoluble in said alcohol, wherein said polyactive hydrogen compound is an alkyl, aryl, or aralkyl structure optionally substituted by N, O, and S; (ii) at least one polyisocyanate, and (iii) at least one polyactive hydrogen compound soluble in said mixture of alcohol and water; (b) a polyfunctional chain extender; and (c) a monofunctional chain terminator; wherein the equivalent ratio of difunctional chain extender to prepolymer isocyanate is 0.60 to 1.20.

26 Claims, No Drawings

POLYURETHANE DISPERSION IN ALCOHOL-WATER SYSTEM

TECHNICAL FIELD

The present invention pertains to a cold seal adhesive composition in the form of a stable polyurethane dispersion in alcohol-water system.

BACKGROUND

Polyurethane is a generic term used to describe polymers prepared by the reaction of a polyfunctional isocyanate with a polyfunctional alcohol to form urethane linkages. The term "polyurethane" has also been used more generically to refer to the reaction products of polyisocyanates with any polyactive hydrogen compound including polyfunctional alcohols, amines, and mercaptans. Polyurethanes are used in a variety of applications including as elastomers, adhesives, coatings, and impregnating agents.

For coating applications, polyurethane polymers can be dispersed in water by incorporating stabilizing groups into their backbone. Anionic, cationic, and non-ionic dispersion stabilizing groups have been used. Various aqueous polyurethane dispersions have been prepared by those skilled in the art. For example, U.S. Pat. No. 3,479,310 (Dieterich et al.) discloses water-dispersed polyurethane polymers suitable for use as waterproof coatings. The polymer is prepared from polyhydroxy compounds, polyisocyanates, optional chain lengthening agents, and a sufficient amount of a component having an ionic salt-type group. U.S. Pat. No. 4,307,219 (Larson) discloses water dispersible polyurethane resin prepared by reaction of hydrophilic diols, hydrophobic diols, diisocyanates, and, optionally, chain extenders. Such a urethane resin can be used as protective coatings, primers, and binders.

Although aqueous dispersions of polyurethanes have been widely disclosed, the inventors are not aware of any references to stable polyurethane dispersions in alcohol-water solvent systems, particularly in the absence of hydrophilic stabilizing moieties. Stable polyurethane dispersions in hydro-alcohol (i.e., alcohol-water) systems are especially difficult for at least two reasons.

First, the addition of lower alcohols (e.g., $C_1$ to $C_4$) to water decreases the surface tension of the solvent system. For example, a 40% by weight ethanol in water system has a surface tension of about 31 dyne/cm compared to a pure water system, which has a surface tension of about 72 dyne/cm at about 20° C. A 60% by weight ethanol in water system has a surface tension of 27 dyne/cm at about 20° C. The reduction in surface tension can affect the ability to self assemble hydrophilic and hydrophobic domains during the dispersion preparation. Secondly, many of the polyurethane components (i.e., the starting reactants) are soluble in hydro-alcohol solvent systems, which result in solutions and not dispersions. Polymer solutions have substantially higher viscosity than polymer dispersions, making the solutions harder to process in certain operations, such as coating and spraying operations. Polymer solutions also tend to achieve lower percent solids when compared to polymer dispersions, making the former less attractive during coating operations and during shipping. Lower solids solutions also require longer drying times than dispersions both because of the greater amount of solvent present and the higher affinity of the polymer for that solvent. Furthermore, the molecular weight of soluble polymers is often much lower than that of dispersions.

U.S. Pat. No. 4,507,430 (Shimada et al.) discloses a water-based polyurethane emulsion that comprises a hydrogenated polyalkadiene polyol component and a polyisocyanate component. Shimada discloses that the materials are useful as an adhesive or coating material for a polyolefin resin, and can be applied wet and dried or bonded by dry lamination requiring heat and pressure. There was no disclosure of polyurethane dispersions in hydro-alcohol solvent system.

U.S. Pat. No. Re. 34,730 (Salatin et al.) discloses waterborne basecoat compositions comprising (a) an anionic polyurethane resin comprised of (i) a polyester resin component produced by reaction of a carboxylic acid component comprised of at least 50% by weight $C_{18-60}$ long chain acid and a polyol and (ii) a mixture of at least one multifunctional compound having at least one active hydrogen functionality and at least one carboxylic acid functionality neutralized with an amine, (b) a polyisocyanate combined with a crosslinking agent, and (c) a rheology control agent. U.S. Pat. No. 5,326,815 (Serdiuk et al.) discloses a coating composition comprising (a) an aqueous medium, (b) a water-dispersible polyurethane resin that is the reaction product of (i) a hydroxy-functional polyester resin component that is the reaction product of a carboxylic acid component comprising at least two carboxylic acids, a $C_{36}$ dimer fatty alcohol, and a short-chain polyol, (ii) a multifunctional compound having at least one active hydrogen group and at least one water-stabilizing group, (iii) an active hydrogen-containing capping or chain extending agent, and (iv) a polyisocyanate, and (c) an aminoplast crosslinking agent. The active hydrogen-containing capping agent is used in excess to terminate the isocyanate functional prepolymer, providing terminal hydroxyl groups for reaction with the crosslinking agent. Other patents describing the use of dimer fatty alcohols or polyesters derived from dimer acid in waterbased polyurethane dispersions for basecoat compositions include U.S. Pat. No. 4,423,179 (Guagliardo), U.S. Pat. No. 5,334,650 (Serdiuk et al.), and U.S. Pat. No. 5,370,910 (Hille et al.). None of the above references disclose a polyurethane dispersion in alcohol-water system.

U.S. Pat. No. 5,672,653 (Frisch et al.) discloses an anionic waterborne polyurethane dispersion prepared by (a) forming a prepolymer from hydroxy terminated polybutadiene resin, an aliphatic isocyanate, and a diol containing acid groups; (b) neutralizing the acid; dispersing it in water; and (c) chain extending the prepolymer with a diamine.

Cold seal properties in adhesives have been discussed by those skilled in the art. For example, U.S. Pat. No. 5,616,400 (Zhang) discloses a sheet material coated with a dry cold seal adhesive consisting essentially of the reaction product of 50 to 80% polyester polyol, 15–25% aliphatic diisocyanate, and 3 to 6% dimethylol propionic acid neutralized with a base, said reaction product having a $T_g$ between about −20° and 5° C. U.S. Pat. No. 5,981,650 (Zhao et al.) discloses an aqueous cold-seal adhesive dispersion containing 30% to 55% of a polyurethane ionomer with a $T_g$ between −50° C. and 10° C., which is the reaction product of a polyester polyol and polyether polyol blend, an aliphatic diisocyanate, and dimethylol propionic acid, with 0.05% to 4% colloidal amorphous silica reacted in situ with an organic NCO containing moiety. The use of an alcohol insoluble oligomeric diol is not disclosed in these patents, nor is the importance of controlling molecular weight through the use of chain terminators to give cold seal adhesive properties.

Water-soluble or water-dispersible polyurethanes have been disclosed for use in cosmetic formulations. EP 656,021 B1 (Son et al.), WO 96/14049 (Emmerling et al.), U.S. Pat. No. 5,643,581 (Mougin et al.), U.S. Pat. No. 5,874,072 (Alwattari et al.), U.S. Pat. No. 5,972,354 (de la Poterie et al.), WO 99/43289 (Ohta et al.), EP 938,889 A2 (Son et al.), and U.S. Pat. No. 5,968,494 (Kukkala et al.) are representative. None use oligomeric alcohol insoluble polyactive hydrogen compounds, such as oligomeric alcohol insoluble diols, in preparing the polyurethane.

None of the technologies discussed above recognize the importance of controlling molecular weight through the use of chain terminators to give cold seal adhesive properties, nor do they suggest the use of these materials in cosmetic or medical formulations.

A need exists in the art for polyurethane dispersions stable in alcohol-water solvent systems, where the dispersion has one or more of the following properties: capable of forming stable dispersions in hydro-alcohol systems, capable of rapidly forming films on skin or hair by simple ambient evaporation, and capable of achieving high solids level. Furthermore, films formed by drying down the dispersions exhibit one or more of the following properties: high self adhesion and yet low tack, low humidity sensitivity, and high tensile strength.

SUMMARY

The present invention provides a novel polyurethane-urea dispersion that can be prepared in the presence of and is dispersed in a hydro-alcohol system. As used herein, the term "hydro-alcohol" refers to solvents based on $C_1$ to $C_4$ lower alcohols mixed with water, wherein the weight ratio of lower alcohol to water is preferably at least 20:80, more preferably at least 40:60, even more preferably at least 60:40 and most preferably at least 70:30 by weight. The preferred lower alcohols include ethanol, 2-propanol, and n-propanol. The term "hydro-alcohol" is synonymous with the term "alcohol-water."

As used herein, "dispersion" means generally a two phase system where one phase contains discrete particles distributed throughout a bulk substance, the particles being the disperse or internal phase, and the bulk substance the continuous or external phase. In this invention, the continuous phase is the alcohol-water mixture and at least a portion of the polyurethane exists as the discrete particle. By "dispersion," it is also meant that not necessarily the entire polyurethane polymer needs to be alcohol-water insoluble; some of the polymer can be soluble in the alcohol-water mixture. Dispersions are possible through the use of certain components that are insoluble in the solvent system. It is desirable that the dispersion remains stable under ambient conditions. Preferred dispersions are stable at room temperature for more than 30 days, preferably more than 90 days, more preferably for more than 180 days, and most preferably for more than 360 days.

In one aspect of the present invention, the molecular weight of the polyurethane polymer is deliberately limited to produce a material that, when coated onto a substrate, forms a film with high cohesive strength, i.e., the adhesion of the film to itself is high. Furthermore, many of these novel formulations have very low adhesion to other surfaces, such as glass.

In brief summary, in one aspect, the invention provides a polyurethane dispersion stable in a mixture of alcohol and water, the dispersion comprising the reaction product of: (a) an isocyanate terminated polyurethane prepolymer comprising the reaction product of (i) at least one polyactive hydrogen compound insoluble in the alcohol, wherein the polyactive hydrogen compound is an alkyl, aryl, or aralkyl structure optionally substituted by N, O, S and combinations thereof (referred to as the "A" component for convenience); (ii) at least one polyisocyanate, and (iii) at least one polyactive hydrogen compound soluble in the mixture of alcohol and water (referred to as the "B" component for convenience); (b) a polyfunctional chain extender; and (c) a chain terminator. In one embodiment, the equivalent ratio of active hydrogen on the chain extender to the prepolymer isocyanate is 0.6:1 to 1.20:1. In another embodiment, the chain terminator is a monofunctional hydroxy or amine.

In a preferred embodiment, the inventive polyurethane dispersion is stable in a mixture of alcohol and water and the dispersion comprises the reaction product of (a) an isocyanate terminated polyurethane prepolymer comprising the reaction product of (i) about 20 to 30 parts by weight hydrogenated polybutadiene diol, (ii) about 15 to 30 parts by weight isophorone diisocyanate, and (iii) about 0 to 10 parts by weight sulfonated polyester diol and (iv) about 25 to 75 parts by weight polytetramethylene oxide diol; (b) about 0.05 to 5 parts by weight ethylene diamine; and (c) about 0 to 5 parts by weight 2-amino-2-methyl-1-propanol.

In yet another embodiment, the inventive polyurethane dispersion is useful as a cold seal adhesive. As used herein, the term "cold seal adhesive" (commonly referred to as "contact adhesive") means the adhesive exhibits good self adhesion properties and is typically non-adhering or only very slightly adhering to chemically dissimilar surfaces at temperatures of about 15° to 50° C. When placed against each other, cold seal adhesives typically require moderate pressure (such as exerted by fingertip pressure) to achieve a bond without the need to use significantly elevated temperatures. That is, a bond may be formed at room temperature (i.e., about 20° to 30° C.) and even lower temperature (e.g., about 15° C.), as well as at temperatures up to about 50° C. Thermal curing or crosslinking agents are typically not needed for the cold seal adhesive to form a bond.

As used herein, a material possesses "self adhesion" properties when it preferentially adheres to itself or a chemically similar material under pressure or force without the need for significantly elevated temperatures (e.g., without the need for temperatures above about 50° C.). Preferred compositions of the invention exhibit self adhesion properties immediately upon contact to itself at room temperature (about 20° to 30° C.). As used in the previous sentence, the term "immediately" means less than a few minutes, e.g., about 5 minutes, preferably less than 1 minute, more preferably less than 30 seconds, depending on the application.

A cold seal adhesive is to be distinguished from a pressure sensitive adhesive (PSA). A PSA typically has tack at room temperature, requires moderate pressure to achieve a bond (such as that exerted by fingertip pressure), and adheres to a wide variety of dissimilar substrates. A PSA is conventionally understood to refer to an adhesive that displays permanent and aggressive tack to a wide variety of substrates after applying moderate pressure. An accepted quantitative description of a PSA is given by the Dahlquist criterion line, which indicates that materials having a storage modulus (G') of less than about $3 \times 10^5$ Pascals (measured at 10 radians/second at a temperature of about 20° to 22° C.) have PSA properties while materials having a G' in excess of this value do not.

The inventive polyurethane dispersions are useful in a variety of applications where cold seal properties are desirable. Such applications include the manufacture of self-seal envelopes; in food packaging applications were heat should be avoided (especially ice cream, sugar cubes, tea bags, baked goods, snacks, milk and dairy products, dried and frozen foods, chocolates and other candies, meats, beverages, condiments/spices, sauces and pet foods); in sealing cartons, bags, and other containers; in bundling tapes; in book binding; in cigarette and detergent packaging; liquid packaging; and twist wraps, medical packaging articles, and adhering medical articles to skin.

An advantage of the inventive composition is the use of an oligomeric alcohol insoluble polyactive hydrogen compound. Because of its hydrophobic nature, such compound provides faster drying and improved hydrolytic stability over prior art synthetic cold seal adhesives. A further advantage of the inventive composition is that it possesses adhesion to low energy substrates similar to that provided by natural rubber-based cold seal adhesives, but without the disadvantages associated with such adhesives. Those disadvantages include discoloration, unpleasant odor, undesirable foaming in wet form, hypersensitivity, and possibility of anaphylactic shock due to the presence of natural latex proteins.

Yet another advantage of the inventive composition is that it has low viscosity and fast drying characteristics in addition to exhibiting self adhesion properties. Thus, the composition is suitable for use as a saturant in processes for preparing cohesive elastomeric bandages such as disclosed in U.S. Pat. No. 4,699,133 (Schafer et al.); U.S. Pat. No. 5,230,701 (Meyer et al.); U.S. Pat. No. 5,692,937 (Zhang); and U.S. Pat. No. 5,843,523 (Mazza et al.); all incorporated herein by reference.

A further advantage of the inventive composition is its ability to form hydrophobic films making it useful in cosmetic applications. Such applications require some amount of water resistance, transfer resistance, or substantivity to skin, nails or hair. The applications include, e.g., makeup cosmetic or protective cosmetic applications such as mascara, foundation, rouge, face powder, eyeliner, eyeshadow, insect repellent, nail polish, skin moisturizer, skin cream and body lotion, lipstick, and sunscreen.

When the inventive dispersion is used in hair care products, such as shampoos and conditioners and the like, the dispersion can provide faster drying. It can also improve the humidity resistance of hair styling agents when used at low levels in combination with other hair styling resins. The hair care products, as described herein, are not "reshapable" hair styling compositions. "Reshapable" hair styling composition means a composition that can be restored or modified without new material or heat being applied. For example, in order to restore or modify the hairstyle in case of "drooping" or loss of setting (dishevelment), no new materials, such as water or any form of fixing agent, or heat are required. The composition can be long lasting, such as 10 to 24 hours, giving rise to a durable styling effect.

In the medical article applications, the skin may be coated with the inventive polyurethane dispersion and allowed to dry to form a film. A medical article also pre-coated with the inventive dispersion may be attached to the film. It is a significant advantage that the inventive composition may be adhered to skin and would not have to be removed repeatedly in applications such as ostomy or wound dressing to prevent skin stripping. The adhesives made from the inventive polyurethane dispersions can also be used in any application where ambient temperature self-sealing is required.

DETAILED DESCRIPTION OF THE INVENTION

In brief summary, the dispersion is made by forming the isocyanate terminated polyurethane prepolymer, chain extending the prepolymer, and chain terminating the prepolymer to yield a polyurethane polymer that is stable and dispersed in an alcohol-water solvent system. Although it is presently preferred to carry out the foregoing steps sequentially, this is not necessary. The order of the steps may be changed and certain steps can be combined, such as chain extension and chain termination or prepolymer formation and chain termination, etc. The steps and the components necessary to carry them out are discussed in detail below. In use, the dispersion is typically coated onto a substrate, such as a liner, dried and cured to form a film.

As used herein the term "isocyanate terminated polyurethane prepolymer" (alternately referred to as "isocyanate functional polyurethane prepolymer") means a reaction product of at least one polyisocyanate and at least one polyactive hydrogen compound (i.e., polyol). In general, the reaction occurs with a molar excess of isocyanate groups to produce an oligomer, which may have urethane, urea, thiourethane functional groups and combinations thereof. The prepolymer can be prepared at an equivalent ratio of isocyanate groups to active hydrogen reactive groups of greater than 1.6, preferably greater than 1.8, and most preferably about 2.0 or greater.

As used herein, a "polyol" includes compounds containing active hydrogen in accordance with the Zerevitanov test described by C. R. Noller, *Chemistry of Organic Compounds,* Chapter 6, pages 121–22 (1957). The term "polyol" further means a compound having an average functionality greater than 1, preferably greater than 1.8, and most preferably about 2.0 or greater but less than about 6, preferably less than about 4, and most preferably about 3 or less. It is understood to include compounds that have (i) alcohol groups on primary, secondary, and tertiary carbon atoms, (ii) primary and secondary amines, (iii) mercaptans, and (iv) mixtures of these functional groups. Accordingly, the inventive polyurethane dispersions can contain urea linkages, e.g., from the reaction of isocyanate functional polyurethanes with amines, these polymers more appropriately being labeled as "polyurethane-ureas." Polyols useful for preparing the prepolymer have a molecular weight of 62 to 10,000, preferably 200 to 5,000, and most preferably from 400 to 3,000.

The "A" component, is preferably present at concentrations of at least 5%, preferably at least 10%, and most preferably at least 20% by weight, based on the total weight of the "A" component, the polyisocyanate, and the "B" component. The latter two components are discussed in detail below. The "A" component is insoluble in the alcohol of the alcohol-water mixture used to form the dispersion. The phrase "insoluble" means generally that at least 1 gram of the compound is not soluble in about 4 grams of alcohol at about 25° C. Certain polyols may require heating to melt to determine whether they or insoluble using this characterization method.

The polyols suitable for use as the "A" component have an alkyl, aryl, or aralkyl structure optionally substituted by N, O, S and combinations thereof in and/or on the chain. The "A" component has a number average molecular weight preferably above about 300, more preferably above about 400, and most preferably above about 500, but preferably below about 10000, more preferably below about 5000 and most preferably below about 3000.

Monomeric polyols, such as the $C_{36}$ dimer fatty alcohol available as PRIPOL 2033 from Uniqema North America, Chicago, Ill., USA, can be used. Oligomeric polyols having, on average, from about 1.6 to about 4 hydroxyl or amino groups are preferred. One type of preferred oligomeric polyol useful as the "A" component is aliphatic polyester polyol based on diacids and/or diols that have greater than 10 carbon atoms and preferably greater than 20 carbon atoms. Commercially preferred polyester polyols are PRIPLAST 3191, 3192, 3196, 3197, 1906, and 1907 from Uniqema North America, Chicago, Ill., USA, which are believed to be based on 36 carbon atom diacid and/or diol. Specific constituents used in preparation of these diols are believed to be: for PRIPLAST 3192—dimer acid, adipic acid, and 1,6-hexane diol; for PRIPLAST 3193—dimer acid and ethylene glycol; for PRIPLAST 3194—dimer acid, adipic acid, and ethylene glycol; for PRIPLAST 3196—dimer acid and 1,6-hexane diol; for PRIPLAST 3197—dimer acid and dimer diol; for PRIPLAST 1906—isophthalic acid and dimer diol; and for PRIPLAST 1907—terephthalic acid and dimer diol. The term "dimer acid" is understood to be a $C_{36}$ diacid formed by dimerization of unsaturated $C_{18}$ fatty acids. The term "dimer diol" is understood to be a $C_{36}$ difunctional polyol formed by hydrogenation of the $C_{36}$ dimer acid. Another preferred oligomeric polyol is hydroxy terminated polyalkadienes including polybutadienes and polyisoprenes. A commercially preferred hydroxy terminated polybutadiene is POLY bd resin from Elf Atochem North America, Philadelphia, Pa., USA.

Yet another preferred oligomeric polyol is hydrogenated polyalkadiene polyols including hydrogenated polyisoprene and hydrogenated polybutadiene, the latter having no less than 19% by weight 1,2-butadiene addition. Commercially preferred hydrogenated polybutadiene diols include KRATON L2203 from Shell Chemical, Houston, Tex., USA and POLYTAIL resins from Mitsubishi Chemical, Tokyo, Japan. A preferred type of oligomeric polyamine is amine terminated butadiene polymers and butadiene-acrylonitrile copolymers. A commercially preferred amine is HYCAR ATBN from B.F. Goodrich, Cleveland, Ohio., USA.

Silicone polyols and perfluoroalkyl functional polyols, when used, preferably should not be present in greater than about 5 weight percentage of the overall composition as their low surface energy properties would be expected to detract from the desired adhesion characteristics based on the teachings of U.S. Pat. No. 5,679,754 (Larson et al.).

In addition to alcohol insoluble polyols, low molecular weight "monomeric" polyols may be used to form the prepolymer. Examples of the monomeric polyols include ethylene glycol, propylene glycol, butylene glycol, hexamethylene glycol, diethylene glycol, 1,1,1-trimethylolpropane, pentaerythritol, aminoethanol, and the like. When used, preferably the amount of the monomeric polyols should be kept low to minimize the viscosity of the prepolymer.

The amounts of the polyol and isocyanate used to form the prepolymer affects the physical and chemical properties of the final polymer. Properties that can be varied include, but are not limited to, ductility, water uptake, tensile strength, modulus, abrasion resistance, minimum film-forming temperature, glass transition temperature, ultraviolet light resistance, and resistance to hydrolysis and color stability. In general, longer chain polyols tend to provide films made from the dispersions that are more ductile and have lower $T_g$, higher elongation, and lower tensile strength. In contrast, shorter chain polyols tend to provide films that have high modulus, greater tensile strength, and higher $T_g$. Aliphatic polyols tend to provide materials with decreased water uptake whereas diols containing heteroatoms in the backbone (e.g., polyether polyols) tend to have increased water uptake. The amount of water left in the film can affect its tensile and elongation properties. When resistance to hydrolysis is important, polyols should be selected that are hydrolytically stable such as polyether and polysiloxane polyols, and polyols based on polyolefin backbones. Polyester polyols may be used that are hydrolytically resistant such as those based on hydrophobic subunits (PRIPLAST polyols from Uniqema), those based on isophthalic acid, as well as polycaprolactone polyols.

Representative polyisocyanates that can be used to form the isocyanate functional polyurethane include aliphatic and aromatic polyisocyanates. Suitable polyisocyanates are preferably aliphatic or cycloaliphatic isocyanates. The aromatic isocyanates are less preferred as they tend to discolor in ultraviolet light making them undesirable in outdoor applications. Particularly preferred diisocyanates include dicyclohexylmethane 4,4'-diisocyanate (commonly referred to as $H_{12}MDI$) and 3,5,5-trimethyl-1-isocyanato-3-isocyanatomethylcyclohexane (commonly referred to as isophorone diisocyanate or IPDI), both available from Bayer Corp., Pittsburgh, Pa., USA, under the trade designations DESMODUR W and DESMODUR I, respectively. Other preferred diisocyanates include (i) tetramethylene diisocyanate, (ii) 1,3-bis(isocyanatomethyl)cyclohexane, (iii) 1,3-bis(1-isocyanato-1-methylethyl)benzene, (iv) diphenylmethane 4,4'-diisocyanate (commonly referred to as MDI), (v) 4,4', 4"-triisocyanatotriphenylmethane, (vi) polymethylene polyphenylene polyisocyanate (commonly referred to as polymeric MDI), (vii) toluene diisocyanate (commonly referred to as TDI), (viii) hexamethylene diisocyanate (commonly referred to as HDI), (ix) dodecamethylene diisocyanate, and (x) m- and p-xylene diisocyanate.

Other useful polyisocyanates include those described in U.S. Pat. No. 3,700,643 (Smith et al.) and U.S. Pat. No. 3,600,359 (Miranda), which are incorporated herein by reference. Mixtures of polyisocyanates can also be used, such as ISONATE 2143L, available from Dow Chemical Co., Midland, Mich., USA.

The polyurethane prepolymer is made alcohol-water dispersible by using a "B" component having at least one alcohol-water soluble polyactive hydrogen compound. That is, the "B" component acts primarily to stabilize the polyurethane dispersion in a water or alcohol-water solvent system. The phrase "alcohol-water soluble" means generally that at least 1 gram of the compound is soluble in about 4 grams of an alcohol-water mixture at about 25° C. Certain compounds may require heating to melt to determine whether they are soluble using this characterization method. The alcohol-water mixture used in this characterization method should be the same alcohol-water mixture used to prepare the hydro-alcohol dispersing medium. Alcohol-water solubility is imparted to this compound by the presence of an ionic group, a moiety capable of forming an ionic group, or a polyester, polyether, or polycarbonate group having a ratio of 5 or less, preferably 4 or less, carbon atoms for each oxygen atom, and mixtures thereof.

When present, the ionic group of the "B" component can be anionic, cationic, or zwitterionic. The cationic groups may originate from the isocyanate or polyol component but most conveniently are added in as a polyol component. The cationic group may be incorporated directly into the prepolymer. For example, a quaternary diol such as VARIQUAT 1215 may be reacted into the prepolymer directly. Alternatively, a precursor group can be reacted into the prepolymer and then be rendered cationic in a subsequent reaction. For example, active hydrogen functional tertiary amines such as methyldiethanolamine and its polyethoxylated adducts may be incorporated into the prepolymer backbone and subsequently protonated with a mineral or organic acid to form an ionic salt or alkylated to form a quaternary ammonium group. Reaction of the incorporated tertiary amine with hydrogen peroxide, propane sultone or lactone gives zwitterionic moieties. Preferred stabilizing cationic components are very water soluble, generally have a solubility in water of at least 1% by weight and preferably in excess of 10% by weight. Preferred stabilizing cationic compounds have the following structure:

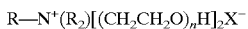

R—N⁺(R$_2$)[(CH$_2$CH$_2$O)$_n$H]$_2$X⁻ where
R is C$_1$ to C$_{18}$ alkyl or C$_6$ to C$_{18}$ aryl or aralkyl optionally substituted in and/or on the chain by N,O, S, and combinations thereof;
R$_2$ is hydrogen or C$_1$ to C$_{18}$ alkyl;
n is an integer from about 1 to 200, preferably 1 to 50, and most preferably 1 to 20; and
X is halogen, sulfate, methosulfate, ethosulfate, acetate, carbonate, or phosphate.

Preferred cationic stabilizing compounds include protonated and alkylated methyl diethanol amine as well as PEG 2 cocomonium chloride and PEG-15 cocomonium chloride available from CK Witco, Greenwich, Conn., USA as VARIQUAT 638 and VARIQUAT K1215 respectively.

It is possible to incorporate cationic compounds that have a single reactive hydrogen group. However, they are less preferred.

The anionic stabilizer used in the present invention can be present on either the isocyanate component or the polyol component. Typically, and most conveniently, the anionic stabilizer is present as the polyol component. The anionic group can be sulfonate, phosphonate, phosphate, and carboxylate but is preferably either sulfonate or carboxylate and most preferably a sulfonate. The most preferred sulfonates are the sulfonated polyols described in U.S. Pat. No. 4,738,992 (Larson et al.). Particularly preferred sulfonates are polyesterdiols having the following structure:

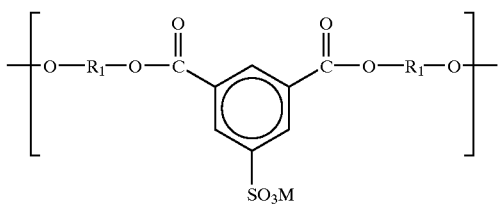

wherein
each R$_1$ is independently a divalent aliphatic group having an average molecular weight of 200 to 600 comprising ether or ester functional groups selected from the group consisting of poly (C$_2$ to C$_4$ alkylene oxide), preferably:
—CH$_2$—CH$_2$—(OCH$_2$—CH$_2$—)$_n$—,
—C(CH$_3$)H—CH$_2$—(OC(CH$_3$)H—CH$_2$—)$_n$—,
—(CH$_2$)$_4$—(O(CH$_2$)$_4$)$_n$—,
—(CH$_2$)$_m$—CO—[—O—(CH$_2$)$_m$—CO—]$_n$—groups, and mixtures thereof,
where m is an integer from about 2 to 5 and n is an integer from about 2 to 15, and M is a cation, preferably M is Na, but M can be H, K, Li, or a primary, secondary, tertiary, or quaternary ammonium cation such as ammonium, methylammonium, butylammonium, diethylammonium, triethylammonium, tetraethylammonium, and benzyltrimethyl-ammonium cation.

Suitable carboxylate and carboxylic acid functional polyols include dimethylolpropionic acid and its polyethoxylated derivatives as well as acid grafted polyethers such as the UCARMOD polyols available from Union Carbide Specialty Chemicals Div., Danbury, Conn., USA. These can be neutralized with an organic or inorganic base either before or after preparation of the prepolymer.

To obtain alcohol-water or water dispersibility, the ionic equivalent weight of the prepolymer (grams prepolymer per equivalent of ionic functionality) should be in the range of 1000 to 15000, preferably 1500 to 12500, more preferably 2000 to 10000, most preferably 2500 to 7500.

Examples of oligomeric polyols that have sufficient polar non-ionic groups such as ether or ester functionality that provides a ratio of 5 or less carbon atoms for each oxygen atom to give alcohol-water solubility include (i) polyoxyalkylene diols, triols, and tetrols, (ii) polyoxyalkylene diamines and triamines, (iii) polyester diols, triols, and tetrols of organic polycarboxylic acids and polyhydric alcohols, and (iv) polylactone diols, triols, and tetrols having a molecular weight of 106 to about 2000. Preferred oligomeric polyols and polyamines include (i) polyethylene oxide homopolymers (e.g., CARBOWAX series from Union Carbide, Danbury, Conn., USA), block copolymers of ethylene oxide and propylene oxide (e.g., PLURONIC surfactants from BASF Corporation, Mount Olive, N.J., USA), random copolymers of ethylene oxide and propylene oxide (e.g., UCON FLUIDS from Union Carbide, Danbury, Conn., USA), silicone copolyols, as well as surfactants based on polyethylene oxide as described in U.S. Pat. No. 4,667,661 (Scholz et al.), (ii) polyoxypropylene diols and triols such as the ACCLAIM series of polyols from Arco Chemical, Newtown Square, Pa., USA, (iii) polyether diamines and triamines such as the JEFFAMINE series available from Huntsman Corporation, Salt Lake City, Utah., USA, (iv) polyether polyols such as the TERATHANE series (which is a polyoxytetramethylene diol) available from E. I. du Pont Co., Wilmington, Del., USA, and the POLYMEG series available from Quaker Oats Co., Chicago, Ill., USA, (v) polyester polyols such as MULTRON, which is a poly (ethyleneadipate)polyol, available from Bayer Corporation, Pittsburgh, Pa., USA, (vi) polycarbonate diols such as those available from Stahl USA Co., Peabody, Mass., USA, and (vii) polycaprolactone polyols such as the TONE series available from Union Carbide, Danbury, Conn., USA. Polythioether polyols are also useful.

The reaction of the components discussed above (i.e., the "A" component, the polyisocyanate, and the "B" component) to form the prepolymer will depend on their selection. Aromatic isocyanates are generally much more reactive than aliphatic isocyanates and may be reacted with polyols without the need for heat because the reaction will be exothermic. The reaction may be run as 100% solids (i.e., little to no solvent) or may be carried out in an optionally polar organic solvent unreactive with the isocyanate. Such solvents include, for example, acetone, methyl ethyl ketone (MEK), methoxypropanol acetate (PM acetate), dimethyl acetamide, tetrahydrofuran, N-methyl-pyrrolidinone and mixtures thereof. Preferably, the solvent used will not require removal in the final composition. It is also possible to incorporate solvents and/or plasticizers that are left in the prepolymer that become part of the finished dispersion.

When using preferred aliphatic isocyanates with polyfunctional alcohols, high solids concentrations and elevated reaction temperatures from about 50° C. to 80° C. are desirable so that high conversions of monomers to polymer can occur in a reasonable time, e.g., less than eight hours, preferably less than three hours. Preferred embodiments incorporating isophorone diisocyanate or hexamethylene diisocyanate and aliphatic primary or secondary alcohols are typically heated to about 80° C. for about 2 hours in the presence of a small amount of catalyst.

Useful catalysts include metal salts such as dibutyltin dilaurate and dibutyltin diacetate, and amines, such as triethylamine, DBU (1,8-diazabicyclo[5.4.0]undec-7-ene), and DABCO (1,4-diazabicyclo[2.2.2]octane), in useful concentrations of from about 0.01 to 1.0 mole percent (relative to the isocyanate reagent). Preferred catalysts are non-irritating and non-sensitizing to skin. Most preferred catalysts are those that can become bound to the polymer backbone and are thus non-leachable, such as FASTCAT 4224 from Elf Atochem North America, Philadelphia, Pa., USA and certain alcohol and amine functional tertiary amine catalysts such as methyldiethanolamine and tetramethylguanidine. In batch preparations from about 100 to 1000 grams, we have typically used about 0.1 gram of FASTCAT 4224 per 100 gram of total resin.

The ratio of polyisocyanate to polyol is adjusted such that the prepolymer has a molecular weight of about 1000 to 25000. The equivalents of polyisocyanate preferably exceed the total equivalents of polyol (i.e., total equivalents of active hydrogen), the equivalent excess being preferably from about 1. 1:1 to 6:1, more preferably about 1.5:1 to 3:1, and most preferably about 1.8:1 to 2.2:1.

Once the prepolymer is formed, the molecular weight should be increased to yield a composition with the desired properties. This step is accomplished by reacting the prepolymer with a "chain extender." As used herein the term "chain extender" means a polyactive hydrogen compound having a functionality of about 2 to 4, more preferably 2 to 3, and most preferably about 2 and generally having a molecular weight of about 30 to 2000, preferably 30 to 1000. Preferred chain extenders are polyfunctional alcohols, amines, or carboxylic acid hydrazides. Most preferred chain extenders are polyfunctional amines and carboxylic acid hydrazides.

Useful polyamines include: ethylenediamine; 1,6-diaminohexane; piperazine; tris(2-aminoethyl)amine; and amine terminated polyethers such as JEFFAMINE D230 and JEFFAMINE D400, from the Huntsman Corporation, Salt Lake City, Utah., USA.

Useful carboxylic acid hydrazides include adipic acid dihydrazide and oxalic acid dihydrazide. Particularly useful polyfunctional alcohols include alkylene diols having 2 to 24 carbon atoms such as ethylene glycol; 1,4-butane diol; and 1,8-octane diol. Useful polythiols include 1,2-ethanedithiol; 1,4-butanedithiol; 2,2'-oxytris(ethane thiol) and di- and tri-mercaptopropionate esters of poly (oxyethylene) diols and triols. Water is also useful as a chain extender as it reacts with isocyanate to form an unstable carbamic acid, which loses carbon dioxide to liberate an amine. This amine is then available to react with another isocyanate.

When the prepolymer has a functionality of 2 or less and the chain extender is difunctional, the ratio of isocyanate to active hydrogen in the chain extension step is preferably from about 0.6:1 to 1.2:1, more preferably from 0.75:1 to 1:1 and most preferably from 0.80:1 to 1:1 (except when water is used as the sole chain extender, in which case water can be present in large molar excess). When the prepolymer has a functionality higher than 2, due to the use of polyols or polyisocyanates with a functionality greater than 2, the ratio of isocyanate to active hydrogen present in the chain extender should be proportionately adjusted downward to prevent gelation and keep the molecular weight of the polyurethane polymer formed in an appropriate range to provide cold seal performance. Also, when the prepolymer has a functionality of 2 or less, some higher functionality chain extender can be used, e.g., a minor amount of trifunctional amine.

The dispersions of the present invention are in water or alcohol-water with relatively high concentrations of a lower alcohol (typically more than 20:80 w/w alcohol to water). In this environment, endcapping of the isocyanate functional prepolymer may occur as the isocyanate reacts with the alcohol solvent. Therefore, use of a polyfunctional amine as the chain extender is preferred because amines are much more reactive toward isocyanate than the lower alcohol, giving better control of molecular weight. For use in skin or hair contact applications where irritation and/or sensitization is a concern, the most preferred ratio of isocyanate equivalents to amine equivalents is about 1:0.60 to 1:0.99 in order to ensure that little to no residual free amine remains in the final dispersion.

The solvent used as the dispersing medium is selected from the group consisting of a lower alcohol ($C_1$ to $C_4$ branched or straight chain aliphatic alcohol), water, and mixtures thereof. The preferred lower alcohols are ethanol, n-propanol, and 2-propanol (IPA). The most preferred solvents are water, IPA, ethanol, and mixtures thereof. Preferably the alcohol to water ratio is 20:80 to 90:10 w/w and more preferably the ratio is 70:30 to 85:15. In general, higher amounts of alcohol will result in a dispersion that exhibits faster dry times.

The solvent system may also comprise additional solvents. For example, other rapid evaporating solvents may be used, such as hexamethyldisiloxane (HMDS); cyclic silicones ($D_4$ and $D_5$); $C_4$–$C_{10}$ alkanes including isoparafins such as Permethyl 97A and Isopar C; acetone; hydrofluoroethers (HFEs) and the like. Certain HFEs, such as HFE 7100, have the added benefit in certain applications. When it is added to hydro-alcohol mixtures in levels above about 15 to 25% by weight, the composition becomes non-flammable.

In one embodiment, the reaction that forms the polyurethane polymer can be stopped by using chain termination species. These species stop the growing polymer chain thereby controlling the molecular weight and the physical properties of the polymer. In one embodiment, a diamine chain extender is used in excess. The excess diamine functions as a chain terminator. Another useful chain terminating agent is 2-amino-2-methyl-1-propanol (AMP), used in about 0.1 to 2.0 parts, based on the total weight of the polyurethane polymer. Monofunctional amines or alcohols are useful as chain terminators. An example of a preferred monofunctional alcohol is ethanol, which can further function as part of the dispersing medium. Chain termination may occur during prepolymer formation, before or after chain extension, or before or after dispersing in solvent mixture. In the present preferred method, an amine chain terminator is mixed with the chain extender and added to the solvent prior to adding the prepolymer.

Preparation of the Dispersion

The dispersions of the present invention may be prepared in any number of methods. In a first method, the prepolymer can be added to the solvent as 100% solids or diluted first with a different solvent that may or may not be removed later. If the solvent is to be removed, it is preferably more volatile than either water or the lower alcohol. In another method, the prepolymer can be dispersed in part of or in all of the solvent mixture or in a portion of the solvent mixture with subsequent addition of additional solvents. Any additional solvent added after dispersion is preferably added slowly in order to ensure the dispersion maintains stability. In yet another method, the prepolymer and/or dispersion solvent may be heated or cooled. In yet another method, the prepolymer may be dispersed in the solvent prior to, simultaneously with, or after the chain extension and chain termination has been added to the solvent mixture.

The preferred dispersion method involves heating the prepolymer to temperatures of about 45° C. to 80° C. to reduce its viscosity. The heated prepolymer is added to a rapidly stirring high shear mixing apparatus, such as a homogenizer, containing the solvent. Thereafter, the amine, a chain extender, is added at a predetermined rate. Alternatively, for certain formulations, the amine can be added to the solvent mixture first and the heated prepolymer added to the rapidly mixing solvent mixture.

For an alcohol-water system, the level of lower alcohol is preferably at least 20% by weight, more preferably at least 40%, even more preferably at least 60%, and most preferably at least 70% by weight. The level of lower alcohol preferably is not more than 90% and more preferably not more than 85%. As used herein, "percent solids" is defined as the percentage of non-volatile components present in the dispersion. For cold seal applications where a uniform continuous 10 to 50 micron coating is desired, the percent solids should be above about 15%, preferably greater than 25%, and most preferably greater than about 40% by weight. For other applications where a lighter or discontinuous coating is desired, percent solids levels down to 2% and less may be advantageously used.

In one aspect of the present invention, films can be produced from the dispersion that have very little adhesion or tack to most surfaces such as skin, hair, and glass but have comparatively high adhesion to themselves. When tested according to the test methods described herein, the ratio of adhesion to self to adhesion to glass is greater than about 2:1, preferably greater than about 3:1, more preferably greater than about 5:1 and most preferably greater than about 10:1. In certain embodiments, the ratio exceeds 20:1 and even 30:1 although such high ratios may not be required for all applications. When used in cold seal applications (which requires very little tack but high self adhesion), the adhesion to glass is preferably less than about 10 Newtons per decimeter (N/dM), more preferably less than about 8 N/dM and most preferably less than about 5 N/dM while the adhesion to self is greater than about 10 N/dM, preferably greater than about 20 N/dM, more preferably greater than about 25 N/dM and most preferably greater than about 30 N/dM.

We have found that one requirement for producing high self adhesive coatings is the molecular weight of the polyurethane in the final dispersion. The preferred weight average molecular weight is about 5000 to 50000, more preferably about 15000 to 35000 and most preferably about 20000 to 30000. When the molecular weight is too high, the resulting adhesive has very little self-adhesion. When the molecular weight is too low, the adhesive tends to have higher tack or adhesion to other substrates.

The molecular weight of the polymer in the final dispersion can be controlled in several ways. The first method concerns the alcohol to water ratio used as the dispersing medium. We have found that for certain polymers, self-adhesion can be achieved at alcohol to water ratios in excess of about 75:25 wt/wt, preferably above 80:20, and more preferably at or above about 85:15. While not wanting to be bound by theory, it is believed that at higher alcohol to water ratios, more of the isocyanate reacts with the monofunctional alcohol solvent, thereby limiting the molecular weight. It is also believed that the higher alcohol ratios result in better solvation and dissolution of the prepolymer thereby also increasing the likelihood of reaction of the isocyanate groups with the monofunctional lower alcohol solvent.

The molecular weight of the prepolymer can also be controlled by the type of alcohol used as the solvent. Primary alcohols may result in higher self-adhesion than secondary alcohol solvents such as isopropanol.

The molecular weight of the prepolymer can be further controlled by the process of dispersion and the process of adding the chain extender. At the current time, we believe that dispersing the prepolymer in the solvent first, followed by amine addition (as the chain extender) at slower rates, can also improve the level of self-adhesion. A slow amine addition rate, however, can increase the level of tack.

The presently preferred method of controlling the level of self-adhesion is with the use of monofunctional amines added prior to or during the chain extension step. This method will result in end capping of some isocyanate groups thereby limiting the molecular weight. The monofunctional amines generally have the following structure:

where $R_1$ and $R_2$ are independently H or $C_1$ to $C_{22}$ alkyl; $C_6$ to $C_{28}$ aryl, or $C_6$ to $C_{28}$ aralkyl optionally substituted in available positions by N, O, and S, including alcohol, tertiary amine, quaternary amine, ketone, and carboxylic acid substitutions. Preferred monofunctional amines are those that would have low skin irritation if left unreacted in the formulation, such as 2-amino-2-methylpropanol or higher alkyl primary and secondary amines as well primary and secondary alkanolamines.

The level of ionic stabilizer may also effect self-adhesion. At the current time, it is believed that higher levels of stabilizer may result in lower self-adhesion.

The formulations of the present invention may also include plasticizers that can be added either to the prepolymer directly or can be added to the solvent mixture. The use of plasticizers may allow for the use of less solvent, and therefore produce more rapidly drying films. Where plasticizers are used, the base prepolymer should be formulated to ensure the plasticized adhesive has sufficient tensile strength. This could require the use of lower molecular weight polyols (lower NCO equivalent weight prepolymers). Preferred plasticizers are cosmetically acceptable emollients such as those disclosed in U.S. Pat. No. 5,951,993 at column, 17 line 35 to column 21, line 6.

Other compounds may be added to enhance or obtain particular properties, provided they do not interfere with the coating, and film forming properties. The dispersion may contain defoaming agents. Particularly useful defoaming agents include, e.g., Surfynol™ DF 110L (a high molecular weight acetylenic glycol nonionic surfactant available from Air Products & Chemicals, Inc.), SWS-211 (a silicone additive available from Wacker Silicone Corp), Dehydran™ 1620 (a modified polyol/polysiloxane adduct available from Henkel Corp.), Additive 65 (a silicone additive available from Dow Corning).

The dispersion may also contain flow and leveling agents such as Igepal™ CO-630 (an ethoxylated nonylphenol nonionic surfactant available from Rhone-Poulenc Surfactant & Specialty Div.), FLUORAD FC-171 (a nonionic surfactant available from 3M Company), FLUORAD FC-430 (a nonionic surfactant available from 3M Company), and Rexol™ 25/9 (an alkyl phenol ethoxylate nonionic surfactant available from Hart Chemical Ltd). Optionally, the dispersion may contain rheology modifiers such as the associative thickeners Acrysol™ RM-825, Acrysol TT-935 all available from Rohm and Haas company.

To increase the service life of the coatings generated from these dispersions, especially in outdoor applications, photostabilizers can be added. Useful photostabilizers include Tinuvin™ 400, (a hindered amine light stabilizer), Tinuvin 292 (a hindered amine light stabilizer), both commercially available from Ciba-Geigy Ltd. Also, antioxidants, such as IRGANOX 245 available from Ciba-Geigy Ltd., and Naugard 445, a 4,4'-bis ($\alpha,\alpha$dimethylbenzyl) diphenylamine, available from Uniroyl Chemicals can be added. For applications subjected to ultraviolet light (UV) degradation, at least about 0.1 parts by weight of the UV light stabilizer per 100 parts by weight polyurethane dispersion can be used to inhibit and retard the yellowing and photo degradation. Typically about 0.1 to 10 parts, preferably about 1 to about 10 parts are used per 100 parts of the polyurethane dispersion.

EXAMPLES

The following examples further illustrate various specific features, advantages, and other details of the invention. The particular materials and amounts recited in these examples, as well as other conditions and details, should not be construed in a manner that would unduly limit the scope of this invention. Percentages given are by weight, unless otherwise specified.

Test Methods

The tack of the inventive adhesives was qualitatively assessed by a "finger appeal" test involving a light touch and short contact time, and assigned a value of 1 through 5, where 1=tack free, 1.25=very, very, low tack, 1.5=very low tack, 2=low tack, 2.5=low-to-medium tack, 3=medium tack, 3.5=medium-to-high tack, 4=high tack, and 5=very high tack. On this scale, SCOTCH MAGIC transparent tape from Minnesota Mining and Manufacturing Co. (3M), St. Paul, Minn., USA has a rating of 5.

A 180° Peel Adhesion is a measure of the force required to remove an adhesive coated, flexible facestock from a substrate after a specified period of dwell and at a specific angle and removal rate. It was determined in accordance with Pressure-Sensitive Tape Council test PSTC #1. In our testing, the face stock is a 0.0015 inch (38 micron) polyester film, the dwell time is one minute (unless otherwise noted), and the pull rate was 12 inches (30.5 cm) per minute. For adhesion to glass, a ½ inch (1.3 cm) by 6 inch (15 cm) strip of tape is placed on a glass plate freshly cleaned with methyl ethyl ketone. The glass plate is secured onto the platform of an I-Mass Peel Tester from Instrumentors, Inc., Strongsville, Ohio., USA. The strip is pressed onto the substrate by rolling twice (once in each opposite direction) with a 4.5 lb (2 kg) rubber roller. After a one (1) minute dwell, one end of the tape is doubled back until it is almost touching itself, making an angle of 180° with the glass plate, and clamped into the jaws of the I-Mass Tester. The average force required to separate the adhesive coated tape from the glass plate is recorded as the adhesion to glass. This force measurement is obtained in units of ounces per half inch and is converted to Newtons per decimeter (N/dm) by multiplying by 2.189 conversion factor.

A sample's adhesion to self is measured by modifying the standard PSTC #1 test by laminating the ½ inch by 6 inch tape to the adhesive coated side of a ¾ inch (1.9 cm) by 8 inch (20 cm) strip of the same tape with two passes of the 2 kg rubber roller. After a one (1) minute dwell, the ¾ inch tape is adhered to the platform of the I-Mass Peel Tester with 3M SCOTCH double coated tape, and the ½ inch taped peeled from it at 180°.

Preparation of the Sulfopolyester Diol Precursors
Sulfopolyester Diol A

A mixture of dimethyl 5-sodiosulfoisophthalate (DMSSIP, 337.3 g, 1.14 mol, from E. I. DuPont de Nemours, Wilmington, Del., USA), diethylene glycol (DEG, 424 g, 3.99 mol, from Aldrich Chemical Co., Milwaukee, Wis., USA), and zinc acetate, (0.82 g, from Aldrich) was heated to about 180° C. and the methanol by-product was distilled from the reaction mixture. After 4.5 hours NMR analysis of the reaction product showed that less than about 1% residual methyl ester was present in the reaction product.

Dibutyltin dilaurate catalyst (1.51 g, 2.4 mmol, from Alfa Chemical Co., Ward Hill, Mass., USA) was added to the above reaction product, the temperature held at about 180° C., and epsilon-caprolactone (650 g, 5.7 mol, from Aldrich) was added portionwise over about a 30 minute period. When addition was complete, the reaction mixture was held at about 180° C. for 4 hours. The product is designated as sulfopolyester diol A Determination of the hydroxyl equivalent weight of the reaction product was done as follows. A 5.12 g sample of the product mixture was dissolved in 20 mL of methyl ethyl ketone (MEK). Isophorone disocyanate (3.13 g, 14.1 mmol, from Aldrich) and dibutyltin dilaurate (0.02 g) were added. The solution was heated for about 4 hours at about 80° C. The solution was cooled to room temperature. A solution of dibutyl amine (4 milliliter (mL) of a 1.72 molar solution in MEK) was added, and the solution stirred for 15 minutes. Then, 20 mL of methanol and 4 to 5 drops of Bromphenol Blue indicator were added, and the solution titrated to a yellow endpoint with 2.17 mL of a 1.0 molar hydrochloric acid solution in water. This corresponds to a hydroxyl equivalent weight of about 218 (theoretical hydroxyl equivalent weight for sulfopolyester diol A is 235).

Sulfopolyester Diol B

A reactor equipped with a mechanical stirrer, nitrogen purge, and distillation apparatus was charged with dimethyl-5-sodiosulfoisophthalate (700 grams, 4.73 equivalents, from Du Pont, Wilmington, Del., USA), 400 molecular weight polyethylene glycol (1947 grams, 9.735 equivalents, from Union Carbide Corp.; Danbury, Conn., USA), and 425 molecular weight polypropylene glycol (1947 grams, 9.184 equivalents, from Arco Chemical Co.; Newton Square, Pa., USA). The reactor was heated to 345° F. (174° C.) and vacuum was applied on the reactor and held for about 1.5 hours. The vacuum was broken with nitrogen. Titanium butoxide (3.6 grams) was added and the mixture was heated to 430° F. (220° C.) and held for 3 hours while collecting methanol. The temperature was then reduced to 345° F (174° C.) and vacuum was applied to the reaction mixture for one hour. The contents were subsequently cooled to 200° F. (93° C.) under nitrogen and drained to yield a clear, colorless liquid polyol. The measured OH equivalent weight of this polyol is 313 g/mole OH (theoretical OH of 305). The theoretical sulfonate equivalent weight of the polyol mixture is 1879 g polymer/mole sulfonate.

Sulfopolyester Diol C

A 5-liter reaction vessel was charged with 4100 g polyethylene glycol-600 (13.67 equivalents) and 505.67 g dimethyl-5-sodiosulfoisophthalate (3.42 equivalents). The materials were dried under full vacuum at 100° C. for 1 hour. Tetrabutyl titanate (0.08 wt %) was subsequently added and the reaction was heated at 220° C. until approximately 85% of the theoretical methanol had been removed. The reaction temperature was reduced to 170° C. and held under vacuum for 1 hour resulting in a clear, light-yellow material. Calculated hydroxyl equivalent weight was 428, calculated sulfonate equivalent weight was 2632.

Examples 1 to 3

Examples 1 to 3 showed how varying the ethanol-water ratio can change the molecular weight, and hence the peel adhesion values, of the polyurethane dispersion.

Into a one-liter reactor was charged the following components to make a 600 gram batch: 120.6 g (1.09 NCO equivalents) isophorone diisocyanate; 147.6 g (0.089 OH equivalents) KRATON L-2203 hydrogenated polybutadiene diol (OH equivalent weight 1660) from Shell Chemical Co., Houston, Tex., USA; 296.4 g (0.291 OH equivalents) TERATHANE 2000 polytetramethylene oxide diol (OH equivalent weight 1020) from E. I. du Pont Co., Wilmington, Del., USA; 6 g (0.05 OH equivalents) SURFYNOL 104 surfactant, a diol, from Air Products, Lehigh Valley, Pa., USA (OH equivalent weight 113.2); and 24 g (0.110 equivalents) of sulfopolyester diol A prepared above. This hazy mixture was heated with stirring under nitrogen to about 80° C and 0.5 g of dibutyl tin dilaurate catalyst was added. An exotherm to about 90.5° C. occurred, and the reaction was continued with stirring for about 2.5 hours at 80±5° C.

Then, 60 g aliquots (theoretically containing 58.5 milliequivalents of residual NCO) of the resulting product were added to 200 mL glass jars containing 1.48 g (49 milliequivalents of amine) ethylene diamine chain extender in 85.5 g ethanol solvent and 4.5 g water solvent (95:5 ratio, Example 1) or 76.5 g ethanol and 13.5 g water (85:15 ratio, Example 2) or 67.5 g ethanol and 22.5 g water (75:25 ratio, Example 3). Stirring at moderate speed yielded a milky white 40 wt % solids dispersion for all. The resulting dispersions were coated onto a 0.0015 inch (38 micron) thick polyester film at a wet coating thickness of about 0.005 inch (127 microns), dried in a 70° C. forced air oven for 10 minutes yielding clear films, then conditioned overnight under constant temperature (about 22° C.) and humidity (about 50% relative humidity). The samples were tested using the test methods described above. Results are shown in Table I below.

TABLE I

Test data for Examples 1 through 3

| Example | EtOH:Water Ratio | Tack | Peel from Glass (N/dM) | Peel from Self (N/dM) |
| --- | --- | --- | --- | --- |
| 1 | 95:5 | 2 | 121 | 108 |
| 2 | 85:15 | 1.5 | 2 | 88 |
| 3 | 75:25 | 1.5 | 0.7 | 71 |

During peel testing of Example 1, it was noted that the sample showed cohesive failure. As stated, cohesive strength is a measure of the adhesion of the film to itself. Thus, Example 1 is not a particularly useful embodiment in cold seal adhesive application. Examples 2 and 3, however, showed low adhesion to glass but rather good adhesion to self making them more useful as cold seal adhesives.

Examples 4 to 8

Examples 4 to 8 showed how varying weight ratio of the chain extender to the chain terminator can affect the molecular weight of the polyurethane dispersion.

Following the procedure used in Example 1, 78.8 g (47.5 milliequiv OH) KRATON L-2203 diol, 157.6 g (154.5 milliequiv OH) TERATHANE 2000 diol, 12.0 g (40 milliequiv OH) sulfopolyester diol B made above, and 51.5 g (464.3 milliequiv NCO) isophorone diisocyanate were charged into a 500 mL reactor and heated with stirring to about 80° C. under nitrogen. About two (2) drops of dioctyl tin dilaurate were added and an exotherm to about 87° C. was noted. After reacting for about 2½ hours, the mixture was cooled slightly and 30 g aliquots (with 22.2 milliequiv theoretical unreacted NCO) were charged into 100 mL jars containing 45 g of 85:15 ethanol to water solutions of ethylene diamine (EDA, chain extender) and 2-amino-2-methyl-1-propanol (AMP, chain terminator) in various ratio. These mixtures were homogenized with an Omni Macro Homogenizer from Omni International, Marietta, Ga., USA. Coating and testing was done as described in Example 1, with results shown in Table II below.

TABLE II

Formulations and Test Data for Examples 4 through 8

| Ex. | Amount of EDA grams (mequiv) | Amount of AMP grams (mequiv) | Tack | Peel from Glass (N/dM) | Peel from Self (N/dM) |
| --- | --- | --- | --- | --- | --- |
| 4 | 0.70 (23.3) | 0 (0) | 1.25 | 5 | 70 |
| 5 | 0.63 (21.0) | 0.21 (2.3) | 1.25 | 19 | 46 |
| 6 | 0.56 (1.87) | 0.41 (4.6) | 1.5 | 24 | 21 |
| 7 | 0.49 (16.3) | 0.62 (7.0) | 2 | 34 | 35 |
| 8 | 0.35 (11.7) | 1.03 (11.6) | 3 | 89 | 86 |

During testing, Example 8 showed cohesive failure.

Examples 9 and 10

Following the procedure used in Example 1, 46.7 g (28.1 milliequiv OH) KRATON L-2203 diol, 93.3 g (91.5 milliequiv OH) TERATHANE 2000 diol, 20.0 g (66.7 milliequiv OH) sulfopolyester diol B made above, and 40 g (360.4 milliequiv NCO) isophorone diisocyanate were charged into a 500 mL reactor and heated with stirring to about 80° C. under nitrogen. One drop of dioctyl tin dilaurate was added and an exotherm to about 82° C. was noted. After reacting for about 2 hours, the mixture was cooled slightly and 30 g aliquots (with 26.1 milliequiv theoretical unreacted NCO) were charged into 100 mL jars containing 45 g of 85:15 ethanol-water solution of 0.81 g or 0.65 g (27 milliequiv) EDA and 0.48 g (5.4 milliequiv) AMP. These mixtures were homogenized with an Omni Macro Homogenizer.

Comparative Examples A and B

Comparative Examples A and B were prepared according to Examples 9 and 10 above respectively, except that the resulting polyurethane dispersion was dispersed in 100% water. Comparative Examples A and B formed cheesy precipitates and could not be coated. ND means "not determined."

TABLE III

Formulations and Test Data

| Ex. | EtOH:Water Ratio | EDA (grams) | AMP (grams) | Tack | Peel from Glass (N/dM) | Peel from Self (N/dM) |
|---|---|---|---|---|---|---|
| Comp. A | 0:100 | 0.81 | 0 | ND | ND | ND |
| Comp. B | 0:100 | 0.65 | 0.48 | ND | ND | ND |
| 9 | 85:15 | 0.81 | 0 | 1.25 | 19 | 100 |
| 10 | 85:15 | 0.65 | 0.48 | 1.25 | 13 | 33 |

Examples 11 to 13

Following the procedure used in Example 1, 36.8 g (22.2 milliequiv OH) KRATON L-2203 diol, 73.6 g (72.2 milliequiv OH) TERATHANE 2000 diol, 40.0 g (133.3 milliequiv OH) sulfopolyester diol B, and 49.6 g (446.8 milliequiv NCO) isophorone diisocyanate were charged into a 500 mL reactor and heated with stirring to about 80° C. under nitrogen. One (1) drop of dioctyl tin dilaurate was added and an exotherm to about 85° C. was noted. After reacting for about 2 hours, the mixture was cooled slightly and 30 g aliquots (with 32.9 milliequiv theoretical unreacted NCO) were charged into 100 mL jars containing 45 g of either water or 85:15 ethanol-water solution of 1.00 g (33 milliequiv) EDA or 0.80 g (26.7 milliequiv) EDA and 0.60 g (6.7 milliequiv) AMP. These mixtures were homogenized with an Omni Macro Homogenizer. The EDA/AMP/100% water solution (Example 11) was fairly well dispersed and formed a rough/hazy coating. Coating and testing on the others was done as described in Example 1. The results are shown in Table IV below, with ND for "not determined."

Comparative Example C

Comparative Example C was prepared similar to Example 12 and dispersed in 100% water solvent system. Comparative C contained the EDA chain extender but no chain terminator. It formed a cheesy precipitate and could not be coated.

TABLE IV

Formulations and Test Data

| Ex. | EtOH:Water Ratio | EDA (grams) | AMP (grams) | Tack | Peel from Glass (N/dM) | Peel from Self (N/dM) |
|---|---|---|---|---|---|---|
| Comp. C | 0:100 | 1.00 | 0 | ND | ND | ND |
| 11 | 0:100 | 0.80 | 0.60 | 1.5 | 0.2 | 2 |
| 12 | 85:15 | 1.00 | 0 | 1.25 | 8 | 0.6 |
| 13 | 85:15 | 0.80 | 0.60 | 1.5 | 23 | 2 |

Examples 14 to 17

Following the procedure used in Example 1, 157.84 g (95.1 milliequiv OH) KRATON L-2203 diol, 315.45 g (309.3 milliequiv OH) TERATHANE 2000 diol, 24.39 g (81.3 milliequiv OH) sulfopolyester diol B, and 103.4 g (931.5 milliequiv NCO) isophorone diisocyanate were charged into a 500 mL reactor and heated with stirring to about 55° C. under nitrogen. Three (3) drops of dioctyl tin dilaurate were added and a slight exotherm was noted. The temperature was raised to about 80° C. and held there for about 2 hours. The mixture was cooled slightly and 90 g aliquots (with 67.2 milliequiv theoretical unreacted NCO) were charged into 500 mL jars containing 135 g of 85:15 ethanol-water solvent system containing EDA and AMP in various ratio. These mixtures were homogenized with an Omni Macro Homogenizer. Coating and testing was done as described in Example 1, with results shown in Table V below.

TABLE V

Formulations and Test Data for Examples 14 through 17

| Ex. | EDA grams (mequiv) | AMP grams (mequiv) | Tack | Peel from Glass (N/dM) | Peel from Self (N/dM) |
|---|---|---|---|---|---|
| 14 | 1.99 (66.3) | 0 (0) | 1.25 | 5 | 39 |
| 15 | 1.88 (62.7) | 0.31 (3.5) | 1.25 | 10.5 | delamination |
| 16 | 1.78 (59.3) | 0.62 (7.0) | 1.5 | 16 | 52 |
| 17 | 1.57 (52.3) | 1.24 (13.9) | 2 | 31 | 19 |

Examples 18 to 21

Following the procedure used in Example 1, 52.55 g (31.7 milliequiv OH) KRATON L-2203 diol, 105.09 g (105.1 milliequiv OH) polyethylene glycol 2000 diol from Aldrich Chemical Co., 8 g (36.7 milliequiv OH) sulfopolyester diol B, and 34.34 g (30.9 milliequiv NCO) isophorone diisocyanate were charged into a 500 mL reactor and heated with stirring to 80° C. under nitrogen. Two (2) drops of dioctyl tin dilaurate were added and an exotherm to 86° C. was noted. The reaction was continued for about 2 hours, then the mixture was cooled slightly and 30 g aliquots (with 20.4 milliequiv theoretical unreacted NCO) were charged into 200 mL jars containing 45 g of either water or 85:15 ethanol-water solvent systems containing EDA and AMP in various ratio. These mixtures were homogenized with an Omni Macro Homogenizer, giving good dispersions in all cases. Coatings were clear and tacky when removed from the oven, but slightly hazy and tack free with no adhesion to glass or self after conditioning overnight.

Examples 22 to 24

Following the procedure used in Example 1, 78.85 g (47.5 milliequiv OH) KRATON L-2203 diol, 157.6 g (157.6 milliequiv OH) polypropylene glycol 2000 diol from EM Science, Gibbstown, N.J., USA, 12.2 g (40.7 milliequiv OH)

sulfopolyester diol B, and 52.25 g (470.7 milliequiv NCO) isophorone diisocyanate were charged into a 500 mL reactor and heated with stirring to 80° C. under nitrogen. Two (2) drops of dioctyl tin dilaurate were added and an exotherm to 81° C. was noted. After reacting for 2 hours, the mixture was cooled slightly and 30 g aliquots (with 22.4 milliequiv theoretical unreacted NCO) were charged into 100 mL jars containing 45 g of 85:15 ethanol-water solvent mixtures containing EDA and AMP in various ratio. These mixtures were homogenized with an Omni Macro Homogenizer. Coating and testing was done as described in Example 1, with results shown in Table VI below.

TABLE VI

Formulations and Test Data for Examples 22 through 24

| Ex. | EDA grams (mequiv) | AMP grams (mequiv) | Tack | Peel from Glass (N/dM) | Peel from Self (N/dM) |
|---|---|---|---|---|---|
| 22 | 0.66 (22.0) | 0 (0) | 1.25 | 18 | 165 |
| 23 | 0.63 (21.0) | 0.10 (1.1) | 1.5 | 23 | Delamination |
| 24 | 0.59 (1.97) | 0.21 (2.4) | 1.5 | 40 | Delamination |

Examples 25 to 28

Following the procedure used in Example 1, 25 g (15.1 milliequiv OH) KRATON L-2203 diol, 50 g (40.5 milliequiv OH) TEXOX 5WL-1400 2470 molecular weight 75/25 ethylene glycol/propylene glycol random copolymer diol from Texaco Chemical, Houston, Tex., USA, 4 g (13.3 milliequiv OH) sulfopolyester diol B, and 15.3 g (137.8 milliequiv NCO) isophorone diisocyanate were charged into a 500 mL reactor and heated with stirring to about 80° C. under nitrogen. One (1) drop of dioctyl tin dilaurate was added and the reaction continued for about 2 hours. The mixture was cooled slightly and 20 g aliquots (with 14.7 milliequiv theoretical unreacted NCO) were charged into 100 mL jars containing 30 g of either water or 85:15 ethanol-water solvent mixture containing 0.42 g (14 milliequiv) EDA or 0.37 g (12.3 milliequiv) EDA and 0.13 g (1.5 milliequiv) AMP. These mixtures were homogenized with an Omni Macro Homogenizer. The 100% water dispersions (Examples 25 and 26) were very viscous. Coating and testing was done as described in Example 1, with results shown in Table VII below.

TABLE VII

Formulations and Test Data for Examples 25 through 28

| Ex. | EtOH:Water Ratio | EDA (grams) | AMP (grams) | Tack | Peel from Glass (N/dM) | Peel from Self (N/dM) |
|---|---|---|---|---|---|---|
| 25 | 0:100 | 0.42 | 0 | 2 | 4 | 64 |
| 26 | 0:100 | 0.37 | 0.13 | 1.5 | 9 | 130 |
| 27 | 85:15 | 0.42 | 0 | 3 | 27 | 55 |
| 28 | 85:15 | 0.37 | 0.13 | 4 | 37 cohesive | 27 |

Example 26 showed cohesive failure during the peel from self test. Example 27 showed partial delamination during the peel from self test. Example 28 showed cohesive failure during both peel tests.

Examples 29 to 31

Following the procedure used in Example 1, 26.4 g (15.9 milliequiv OH) KRATON L-2203 diol, 36.5 g (182.5 milliequiv OH) 400 molecular weight polyethylene glycol diol from Aldrich Chemical, 4.8 g (16.0 milliequiv OH) sulfopolyester diol B, and 31.1 g (280.2 milliequiv NCO) isophorone diisocyanate were charged into a 500 mL reactor and heated with stirring to about 80° C. under nitrogen. One (1) drop of dioctyl tin dilaurate was added and an exotherm to about 97° C. was noted. The reaction continued for about 1 hour during which time the viscosity increased.

The mixture was cooled slightly and 20 g aliquots (with 13.3 milliequiv theoretical unreacted NCO) of the thick paste were charged into 100 mL jars containing 30 g of either water or 85:15 ethanol-water solution of 1.86 g (62.0 milliequiv) EDA or 1.66 g (55.3 milliequiv) EDA and 0.58 g (6.5 milliequiv) AMP. These mixtures were homogenized with an Omni Macro Homogenizer. The thick paste could not be dispersed in water, but could be dispersed with difficulty in ethanol-water and yielded grainy coatings. Coating and testing was done as described in Example 1, with results shown in Table VIII below.

TABLE VIII

Formulation and Test Data for Examples 29 through 31

| Ex. | EtOH:Water Ratio | EDA (grams) | AMP (grams) | Tack | Peel from Glass (N/dM) | Peel from Self (N/dM) |
|---|---|---|---|---|---|---|
| 29 | 0/100 | 1.86 | 0 | ND | ND | ND |
| 30 | 85/15 | 1.86 | 0 | 3 | 4 | 9 |
| 31 | 85/15 | 1.66 | 0.58 | 4 | 20 | 33 |

Examples 32 to 37

Following the procedure used in Example 1, 40.4 g (24.3 milliequiv OH) KRATON L-2203 diol, 80.7 g (65.3 milliequiv OH) TEXOX WL-1400 2470 molecular weight 75/25 ethylene glycol/propylene glycol random copolymer diol from Texaco Chemical, 6 g (13.3 milliequiv OH) sulfopolyester diol C, and 23.1 g (208.1 milliequiv NCO) isophorone diisocyanate were charged into a 500 mL reactor and heated with stirring to about 80° C. under nitrogen. One (1) drop of dioctyl tin dilaurate was added and the reaction exothermed to about 82° C.

After reacting for about 2 hours, the mixture was cooled slightly and 20 g aliquots (with 14.0 milliequiv theoretical unreacted NCO) were charged into 100 mL jars containing 30 g of either water or 85:15 ethanol-water solution of 0.40 or 0.41 g (13.3 or 13.7 milliequiv, respectively) EDA or 13.9 g (13.9 milliequiv) JEFFAMINE ED2001 2000 molecular weight polyethylene oxide diamine from Huntsman Corporation, Salt Lake City, Utah., USA. TWEEN 40 and STANDAPOL ES2 surfactants were added at 2 wt. % actives to selected dispersions. These mixtures were homogenized with an Omni Macro Homogenizer. All samples had good dispersions. Coating and testing was done as described in Example 1, with results shown in Table IX below.

TABLE IX

Formulations and Test Data for Examples 32 through 37

| Ex. | EtOH:Water Ratio | Diamine (grams) | Surfactant | Tack | Peel from Glass (N/dM) | Peel from Self (N/dM) |
|---|---|---|---|---|---|---|
| 32 | 0:100 | 0.40 EDA | None | 2 | 16 | 56 |
| 33 | 0:100 | 0.40 EDA | Tween 40 | 2.5 | 15 | 50 |
| 34 | 0:100 | 0.40 EDA | Standapol ES2 | 2 | 10 | 43 |
| 35 | 0:100 | 13.9 Jeffamine | None | 3.5 | 30 | 25 |
| 36 | 85:15 | 0.40 EDA | None | 4 | 28 | 18 |
| 37 | 85:15 | 0.41 EDA | None | 4 | 5 | 3 |

Examples 38 to 41

Following the procedure used in Example 1, 78.8 g (47.5 milliequiv OH) KRATON L-2203 diol, 157.5 g (154 milliequiv OH) TERATHANE 2000 diol (T-2000), 12.2 g (40.7 milliequiv OH) sulfopolyester diol B, and 51.6 g (464 milliequiv NCO) isophorone diisocyanate were charged into a 500 mL reactor and heated with stirring to about 60° C. under nitrogen. 3 drops of dibutyl tin dilaurate was added and an exotherm to about 77° C. was noted. The reaction temperature was increased to 80° C. and held there for about 2 hours.

The mixture was cooled slightly and 50 g aliquots (with 40.0 milliequiv theoretical unreacted NCO) of the prepolymer were charged with stirring into 200 mL jars containing 60 g of a 85/15 ethanol/water mixture. A mixture of 1.04 g (34.7 milliequiv) EDA and with 1.9 mequiv of various amine terminators in 15 g of 85:15 ethanol-water were charged in one portion after the prepolymer is well dispersed. Specific amine terminators used were 0.17 g 2-amino-2-methyl-1-propanol (Example 38), 0.36 g dodecyl amine (Example 39), 0.52 g octadecyl amine (Example 40), and 0.77 g didodecyl amine (Example 41). Coating and testing was done as described in Example 1, with results shown in Table X below.

TABLE X

Formulations and Test Data for Examples 38 through 41

| Ex. | Terminator | Tack | Peel from Glass (N/dM) | Peel from Self (N/dM) |
|---|---|---|---|---|
| 38 | AMP | 1.5 | 1.3 | 22.5 |
| 39 | C12 amine | 1.5 | 0.9 | 18.2 |
| 40 | C18 amine | 1.5 | 1.8 | 32.8 |
| 41 | di-C12 amine | 1.5 | 4.7 | 41.2 |

Examples 42 to 45

Following the procedure used in Examples 38 through 41, 77.0 g (76.9 milliequiv OH) PRIPLAST 3197, a 2000 molecular weight polyester diol of dimer diacid and dimer diol from Uniqema, 154.0 g (151 milliequiv OH) TERATHANE 2000 diol, 12.2 g (40.7 milliequiv OH) sulfopolyester diol B, and 56.8 g (511 milliequiv NCO) isophorone diisocyanate were reacted and dispersed in the identical fashion.

TABLE XI

Formulations and Test Data for Examples 42 through 45

| Ex. | Terminator | Tack | Peel from Glass (N/dM) | Peel from Self (N/dM) |
|---|---|---|---|---|
| 42 | AMP | 1.5 | 3.7 | 62.6 |
| 43 | C12 amine | 2 | 3.9 | 67.2 |
| 44 | C18 amine | 1.5 | 3.9 | 69.2 |
| 45 | di-C12 amine | 1.5 | 5.0 | 47.1 |

Examples 46 to 49

Following the procedure used in Examples 38 through 41, 78.8 g (47.5 milliequiv OH) KRATON L2203 diol, 154.0 g (152 milliequiv OH) 2200 molecular weight polypropylene glycol (PPG 2200), 12.2 g (40.7 milliequiv OH) sulfopolyester diol B, and 51.6 g (464 milliequiv NCO) isophorone diisocyanate were reacted and dispersed in the identical fashion.

TABLE XII

Formulations and Test Data for Examples 46 through 49

| Ex. | Terminator | Tack | Peel from Glass (N/dM) | Peel from Self (N/dM) |
|---|---|---|---|---|
| 46 | AMP | 2 | 21.7 | 117.3 |
| 47 | C12 amine | 3 | 19.7 | 80.8 |

TABLE XII-continued

Formulations and Test Data for Examples 46 through 49

| Ex. | Terminator | Tack | Peel from Glass (N/dM) | Peel from Self (N/dM) |
|---|---|---|---|---|
| 48 | C18 amine | 3 | 20.4 | 107.3 |
| 49 | di-C12 amine | 3 | 28.9 | 121.9 |

Examples 50 to 55

The prepolymers prepared for Examples 38 through 41 and 46 through 49 (with Terathane 2000 or PPG 2200 respectively) were reacted with varying amounts of ethylene diamine and aminomethylpropanol as shown in Table XIII below.

TABLE XIII

Formulations and Test Data for Examples 50 through 55

| Ex. | Diol | EDA (grams) | AMP (grams) | Tack | Peel from Glass (N/dM) | Peel from Self (N/dM) |
|---|---|---|---|---|---|---|
| 50 | T2000 | 0.98 | 0.36 | 1.5 | 6.8 | 60.2 |
| 51 | T2000 | 1.02 | 0.30 | 1 | 3.3 | 63.9 |
| 52 | T2000 | 1.00 | 0.23 | 1.25 | 4.4 | 44.4 |
| 53 | PPG2200 | 0.97 | 0.36 | 4 | 45.8 | 108.8 |
| 54 | PPG2200 | 0.99 | 0.23 | 3 | 25.4 | 102.7 |
| 55 | PPG2200 | 1.02 | 0.16 | 2.5 | 4.2 | 72.5 |

Examples 56 to 59

Following the procedure used in Example 1, 25.6 g (20.5 milliequiv OH) polybutadiene polyol with an OH equivalent weight of 1250 and an average functionality greater than 2 sold under the tradename POLY bd by Elf Atochem, Philadelphia, Pa., 51.4 g (51.4 milliequiv OH) TERATHANE 2000 diol, 4.2 g (13.4 milliequiv OH) sulfopolyester diol B, and 18.9 g (170 milliequiv NCO) isophorone diisocyanate were charged into a 250 mL reactor and heated with stirring to about 60° C. under nitrogen. Two (2) drops of dioctyl tin dilaurate was added and an exotherm to about 71° C. was noted. The reaction temperature was increased to 80° C. and held there for about 2 hours.

The mixture was cooled slightly and 20 g aliquots (with 16.9 milliequiv theoretical unreacted NCO) of the prepolymer were charged with stirring into 100 mL jars containing 30 g of a 85/15 ethanol/water mixture containing varying amounts of EDA and AMP. Coating and testing was done as described in Example 1, with results shown the table below.

TABLE XIV

Formulations and Test Data for Examples 56 through 59

| Ex. | EDA (grams) | AMP (grams) | Tack | Peel from Glass (N/dM) | Peel from Self (N/dM) |
|---|---|---|---|---|---|
| 56 | 0.35 | 0.45 | gelled | ND | ND |
| 57 | 0.3 | 0.6 | gelled | ND | ND |
| 58 | 0.25 | 0.75 | 2 | 98.3 | 174.7 |
| 59 | 0.2 | 0.9 | 2 | 143.0 coh | 124.3 |

Examples 60 to 79

Following the procedure used in Example 1, KRATON L-2203 diol and TERATHANE 2000 diol were reacted at various ratios with isophorone diisocyanate (IPDI) and assorted stabilizers including VARIQUAT K1215 cationic diol from Witco, 600 molecular weight polyethylene glycol, dimethylol propanic acid (DMPA), sulfopolyester diol B, or with no additional added stabilizer. The prepolymers were dispersed into ethanol water containing EDA chain extender and AMP chain terminator as detailed below. Coating and testing was done as described in Example 1, with results also shown in Table XV.

TABLE XV

Formulations and Test Data for Examples 60 through 79

| | Prepolymer | | | | Dispersion | | | | | |
|---|---|---|---|---|---|---|---|---|---|---|
| Ex. | KRATON (grams) | TERATHANE (grams) | Stabilizer (grams) | IPDI (grams) | EDA | AMP | ethanol/water ratio | Tack | Peel from Glass (N/dM) | Peel from Self (N/dM) |
| 60 | 39.0 | 76.6 | 9 g Variquat | 26.3 | 0.71 | 0 | 85/15 | 1.5 | 4.4 | 40.5 |
| 61 | 39.0 | 76.6 | 9 g Variquat | 26.3 | 0.64 | 0.21 | 85/15 | 1.5 | 21.9 | 60.4 |
| 62 | 39.0 | 76.6 | 9 g Variquat | 26.3 | 0.57 | 0.41 | 85/15 | 1.5 | 6.1 | 32.0 |
| 63 | 34.0 | 69.4 | 15 g PEG 600 | 20.7 | 0.84 | 0 | 85/15 | 1.5 | 5.9 | 55.4 |
| 64 | 34.0 | 69.4 | 15 g PEG 600 | 20.7 | 0.76 | 0.25 | 85/15 | 1.5 | 6.8 | 24.7 |
| 65 | 34.0 | 69.4 | 15 g PEG 600 | 20.7 | 0.67 | 0.5 | 85/15 | 1.5 | 13.8 | 23.0 |
| 66 | 38.3 | 76.5 | 3 g DMPA | 32.2 | 0.87 | 0.4 | 85/15 | 1 | 0.4 | 0.9 |
| 67 | 38.3 | 76.5 | 3 g DMPA | 32.2 | 0.78 | 0.66 | 85/15 | 1 | 0.7 | 1.3 |
| 68 | 38.3 | 76.5 | 3 g DMPA | 32.2 | 0.7 | 0.92 | 85/15 | 1 | 1.1 | 2.0 |
| 69 | 28.2 | 55.8 | 0 | 16.2 | 0.59 | 0.2 | 100/0 | 1.25 | 0.4 | 1.3 |
| 70 | 28.2 | 55.8 | 0 | 16.2 | 0.59 | 0.2 | 85/15 | 1.25 | 0.2 | 5.0 |
| 71 | 57.3 | 28.7 | 0 | 14 | 0.38 | 0 | 100/0 | 1 | 0.0 | 0.9 |
| 72 | 57.3 | 28.7 | 0 | 14 | 0.3 | 0.22 | 100/0 | 1 | 0.2 | 0.0 |
| 73 | 21.2 | 21.2 | 0 | 7.6 | 0.33 | 0.24 | 100/0 | 1 | 0.7 | 0.9 |
| 74 | 21.2 | 21.2 | 0 | 7.6 | 0.33 | 0.24 | 85/15 | 1 | 0.0 | 0.0 |
| 75 | 8.3 | 33.2 | 0 | 8.5 | 0.36 | 0.27 | 85/15 | 1 | 0.0 | 0.7 |
| 76 | 4.1 | 37.1 | 0 | 8.8 | 0.38 | 0.28 | 85/15 | 1 | 0.2 | 2.8 |
| 77 | 4.1 | 37.1 | 0 | 8.8 | 0.38 | 0.28 | 70/30 | 1.25 | 9.2 | 71.8 |
| 78 | 3.8 | 34.6 | 2 g | 9.6 | 0.41 | 0.31 | 85/15 | 1.25 | 0.0 | 13.4 |

TABLE XV-continued

Formulations and Test Data for Examples 60 through 79

| | Prepolymer | | | Dispersion | | | | | |
|---|---|---|---|---|---|---|---|---|---|
| Ex. | KRATON (grams) | TERATHANE (grams) | Stabilizer (grams) | IPDI (grams) | EDA | AMP | ethanol/water ratio | Tack | Peel from Glass (N/dM) | Peel from Self (N/dM) |
| 79 | 3.8 | 34.6 | Sulfopolyester diol B 2 g Sulfopolyester diol B | 9.6 | 0.41 | 0.31 | 70/30 | 1.25 | 2.2 | 53.4 |

Cosmetic Example 1

A body lotion suitable for use as a waterproof sunscreen or insect repellent with added active ingredients was prepared. An oil-in-water emulsion was prepared using the specific components and amounts in weight percent for Phase A and Phase B listed in Table XVI. Phase A and Phase B were heated to 70° C. with continuous stirring in separate vessels. Phase B was added to Phase A and homogenized using a high shear mixer. Cooling to room temperature with slight agitation yields a moderate viscosity cream.

TABLE XVI

Oil-in-water emulsion for body lotion

| Component | Amount (weight percent) |
|---|---|
| Phase A | |
| Mineral oil | 10.0 |
| Isopropyl myristate | 2.0 |
| Stearic acid | 4.0 |
| Glycerol stearate | 3.0 |
| Ceteth-20 | 1.0 |
| Lanolin oil | 0.6 |
| Dispersion from Example 16 | 2.4 |
| Phase B | |
| Deionized water | 76.8 |
| Hydroxyethyl cellulose | 0.2 |
| Triethanol amine | 1.2 |

Cosmetic Example 2

An oil in water emulsion for mascara was prepared using the specific components and amounts in weight percent for Phase A and Phase B listed in Table XVII. Phase A and Phase B were heated to 90° C. with continuous stirring in separate vessels. Phase B was added to Phase A and homogenized using a high shear mixer. After cooling, the resulting paste provides a flake-, smudge-, and water-resistant mascara.

TABLE XVII

Oil-in-water emulsion for mascara

| Component | Amount (weight percent) |
|---|---|
| Phase A | |
| Carnuba wax | 10.0 |
| Isopropyl myristate | 6.0 |
| Stearic acid | 5.0 |
| Glycerol stearate | 3.0 |
| Dispersion from Example 16 | 6.0 |
| Black iron oxide pigment | 10.0 |
| Phase B | |
| Deionized water | 57.5 |
| Polyvinylpyrrolidone | 1.0 |
| Hydroxyethyl cellulose | 0.2 |
| Triethanol amine | 1.3 |

Cosmetic Example 3

A conditioning shampoo was prepared by charging 35.7 wt. % ammonium lauryl sulfate (28% solids), 24 wt. % ammonium laureth-2-sulfate (25% solids), 3 wt. % ethylene glycol distearate, 1 wt. % cocamide MEA, and 31.2 wt. % deionized water into a vessel. The resulting mixture was heated to 80° C. with stirring and a mixture containing 5 wt. % of the dispersion of Example 16 in 5 wt % of $C_{12}$ to $C_{15}$ alkyl benzoate was added. After cooling, the resulting pearly liquid provides a shampoo with good wet combability after rinsing and fast drying.

Cosmetic Example 4

A clear nail lacquer was made as follows: About 20 parts of a 20% solids ethanol solution of an acrylate grafted silicone copolymer available from 3M Corporation, St. Paul, Minn. under the trade designation VS 80 Silicones Plus copolymer was combined with 1 part of the dispersion solution from Example 16. This provided a fast drying clear nail lacquer with good chip resistance and gloss.

Cosmetic Example 5

A shampoo was prepared by charging 36 wt. % ammonium lauryl sulfate (28% solids), 24 wt. % ammonium laureth-2-sulfate (25% solids), 3 wt. % ethylene glycol distearate, 1 wt. % cocamide MEA, and 6 wt. % deionized water into a vessel. The resulting mixture was heated to 80° C. with stirring to form a pearly liquid. After cooling, 30 wt. % of the 40% solids dispersion of Example 36 was added to provide a shampoo that has a foamy lubricious feel when used at 0.5 milliliters on a 2 gram swatch of hair and gives good wet combability after rinsing and fast drying.

Cosmetic Example 6

A shampoo was prepared by charging 50 wt. % ammonium lauryl sulfate (28% solids), 11 wt. % disodium cocoamphodiacetate (50% solids), and 9 wt. % deionized water into a vessel. The resulting mixture was heated to 80° C.

with stirring to form a clear liquid. After cooling, 30 wt. % of the 40% solids dispersion of Example 36 was added to provide a milky shampoo that has a foamy lubricious feel when used at 0.5 milliliters on a 2 gram swatch of hair and gives good wet combability fast drying.

Cosmetic Example 7

A shampoo was prepared by charging 39 wt. % ammonium lauryl sulfate (28% solids), 11 wt. % cocamidopropyl betaine (35% solids), and 20 wt. % deionized water into a vessel. The resulting mixture was heated to 80° C. with stirring to form a clear liquid. After cooling, 30 wt. % of the 40% solids dispersion of Example 36 was added to provide a shampoo that has a foamy lubricious feel when used at 0.5 millimeters on a 2 gram swatch of hair and gives good wet combability after rising and fast drying.

Cosmetic Examples 8 through 19

Using the same ingredients and procedure as Cosmetic Example 7, the amounts of polymer dispersion and water were varied to give polymer contents ranging from 0.5 to 11 weight % as shown in the Table below.

| Example | Wt. % Dispersion of Ex. 36 | Wt % Water | % Polymer |
| --- | --- | --- | --- |
| 8 | 1.2 | 48.8 | 0.5 |
| 9 | 2 | 48 | 1 |
| 10 | 5 | 45 | 2 |
| 11 | 8 | 42 | 3 |
| 12 | 10 | 40 | 4 |
| 13 | 12 | 38 | 5 |
| 14 | 15 | 35 | 6 |
| 15 | 18 | 32 | 7 |
| 16 | 20 | 30 | 8 |
| 17 | 22 | 28 | 9 |
| 18 | 25 | 25 | 10 |
| 19 | 28 | 22 | 11 |

All references cited herein are incorporated by reference, in each reference's entirety.

What is claimed is:

1. A polyurethane dispersion stable in a mixture of alcohol and water, said dispersion comprising the reaction product of:
   (a) at least one isocyanate terminated polyurethane prepolymer comprising the reaction product of (i) at least one polyactive hydrogen compound insoluble in said alcohol, wherein said polyactive hydrogen compound is an alkyl, aryl, or aralkyl structure optionally substituted by N, O or S or combinations thereof in or on the chain; (ii) at least one polyisocyanate, and (iii) at least one polyactive hydrogen compound soluble in said mixture of alcohol and water,
   (b) at least one polyfunctional chain extender;
   (c) at least one chain terminator; and
   (d) water.

2. The polyurethane dispersion of claim 1, wherein the equivalent ratio of said chain extender to said prepolymer isocyanate is 0.60:1 to 1: 1.2.

3. The polyurethane dispersion of claim 1, wherein the chain terminator is monofunctional.

4. The dispersion of claim 1, wherein component (a)(i) is selected from the group consisting of oligomeric polyols and oligomeric polyamines having on average from about 1.6 to 4 hydroxyl and/or amino groups.

5. The dispersion of claim 1, wherein component (a)(i) is selected from the group consisting of polybutadiene polyols, polyisoprene polyols, hydrogenated polybutadiene polyols, hydrogenated polyisoprene polyols, polyester polyols from dimer diacids, polyester polyols from dimer diols, dimer diols, and combinations thereof.

6. The dispersion of claim 1 comprising at least 5% by weight of component (a)(i) based on the total weight of the a(i), a(ii), and a(iii) components.

7. The dispersion of claim 1, wherein said polyisocyanate is selected from the group consisting of dicyclohexylmethane 4,4'-diisocyanate; 3,5,5-trimethyl-1-isocyanato-3-isocyanatomethylcyclohexane; tetramethylene diisocyanate; 1,3-bis(isocyanatomethyl)cyclohexane; 1,3-bis(1-isocyanato-1-methylethyl)benzene; diphenylmethane 4,4'-diisocyanate; 4,4',4"-triisocyanatotriphenylmethane; polymethylene polyphenylene polyisocyanate; toluene diisocyanate; hexamethylene diisocyanate; dodecamethylene diisocyanate; m- and p-xylene diisocyanate, and combinations thereof.

8. The dispersion of claim 1, where component (a)(iii) is selected from the group consisting of (i) a compound containing an ionic group, (ii) a compound containing a moiety capable of forming an ionic group, (iii) a compound containing a polyester, polyether, or polycarbonate group having a ratio of 5 or less carbon atoms for each oxygen atom; and (iv) mixtures thereof.

9. The dispersion of claim 8, wherein component (a)(iii) is a cationic compound having the following structure:

wherein

R is $C_1$ to $C_{18}$ alkyl or $C_6$ to $C_{18}$ aryl or aralkyl optionally substituted in and/or on the chain by N, O or S or combinations thereof;

$R_2$ is hydrogen or $C_1$ to $C_{18}$ alkyl;

n is an integer from 1 to 200; and

X is halogen, sulfate, methosulfate, ethosulfate, acetate, carbonate, or phosphate.

10. The dispersion of claim 8, wherein component (a)(iii) is a compound having the following structure:

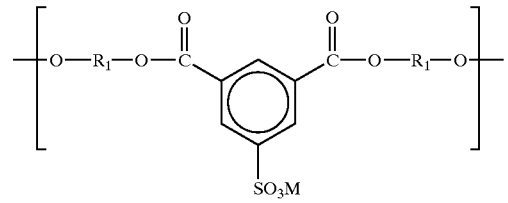

wherein each $R_1$ is independently a divalent aliphatic group having an average molecular weight of 200 to 600 comprising ether or ester functional groups selected from the group consisting of
—$CH_2$—$CH_2$—($OCH_2$—$CH_2$—)$_n$—,
—$C(CH_3)H$—$CH_2$—($OC(CH_3)H$—$CH_2$—)$_n$—,
—$(CH_2)_4$—$(O(CH_2)_4)_n$—,
—$(CH_2)_m$—CO—[—O—$(CH_2)_m$—CO—]$_n$— groups;
and mixtures thereof;

where m is an integer from 2 to 5 and n is an integer from 2 to 15; and

M is selected from the group consisting of Na, H, K, Li, ammonium, methylammonium, butylammonium, diethylammonium, triethylammonium, tetraethylammonium, and benzyltrimethyl-ammonium cation.

11. The dispersion of claim 1, wherein said chain extender is selected from the group consisting of water; ethylenediamine; 1,6-diaminohexane; piperazine; tris(2-aminoethyl) amine; amine terminated polyethers; adipic acid dihydrazide; oxalic acid dihydrazide; ethylene glycol; 1,4 butane diol; 1,8 octane diol; 1,2-ethanedithiol; 1,4-butanedithiol; 2,2'-oxytris(ethane thiol); and di- and tri-mercaptopropionate esters of poly(oxyethylene) diols and triols.

12. The dispersion of claim 1, wherein said polyurethane dispersion has an ionic content of about 1000 to 15000 gram of prepolymer per equivalent of ionic group.

13. The dispersion of claim 1, wherein said reaction product has a weight average molecular weight of about 5000 to 50000.

14. The dispersion of claim 1, wherein said dispersion further comprises a lower alcohol.

15. The dispersion of claim 14, wherein said lower alcohol is selected from the group consisting of ethanol, n-propanol, 2-propanol, and combinations thereof.

16. The dispersion of claim 14, wherein said composition comprises at least 20% by weight of said lower alcohol based on the total composition weight.

17. A cold seal adhesive comprising the dispersion of claim 1.

18. The adhesive of claim 17 exhibiting self-adhesion properties when coated and dried to a film of about 0.025 millimeter in thickness.

19. The adhesive of claim 17 having an adhesion to self value greater than 5 Newtons per decimeter.

20. The adhesive of claim 17 having an adhesion to glass value less than 10 Newtons per decimeter.

21. A product comprising the dispersion of claim 1, the product selected from the group consisting of self-seal envelopes, bundling tapes, heat sensitive products, containers, text binders, medical products, packaging material for medical products, and diaper closures.

22. A saturant in a cohesive elastomeric bandage compring the dispersion of claim 1.

23. A cosmetic application comprising the dispersion of claim 1, the cosmetic application selected from the group consisting of mascara, foundation, rouge, face powder, eye liner, eye shadow, lipstick, insect repellent, nail polish, skin moisturizer, skin cream, body lotion, and sunscreen.

24. A hair care composition comprising the dispersion of claim 1, the hair care composition selected from the group consisting of shampoos, conditioners, hair sprays, mousses, and gels and wherein said hair care composition is not a resphapeable hair styling composition.

25. The dispersion of claim 1 further comprising an additive selected from the group consisting of defoaming agents, flow and leveling agents, rheology modifiers, photostabilizers, and combinations thereof.

26. A polyurethane dispersion stable in a mixture of alcohol and water, said dispersion comprising the reaction product of:

(a) an isocyanate terminated polyurethane prepolymer comprising the reaction product of (i) about 20 to 30 parts by weight hydrogenated polybutadiene diol, (ii) about 15 to 30 parts by weight isophorone diisocyanate, and (iii) about 0 to 10 parts by weight sulfonated polyester diol and about 25 to 75 parts by weight polytetramethylene oxide diol;

(b) about 0.05 to 5 parts by weight ethylene diamine;

(c) about 0 to 5 parts by weight 2-amino-2-methyl-1-propanol; and (d) water.

* * * * *